(12) United States Patent
Cranin et al.

(10) Patent No.: US 10,378,875 B2
(45) Date of Patent: Aug. 13, 2019

(54) PERFORMANCE GAUGE FOR FABRIC AND CUSHIONING MATERIAL

(71) Applicants: Jonathan Cranin, New York, NY (US); Deepa Thomas, San Francisco, CA (US); Matthew Thomas, Portola Valley, CA (US)

(72) Inventors: Jonathan Cranin, New York, NY (US); Deepa Thomas, San Francisco, CA (US); Matthew Thomas, Portola Valley, CA (US)

( * ) Notice: Subject to any disclaimer, the term of this patent is extended or adjusted under 35 U.S.C. 154(b) by 0 days.

(21) Appl. No.: 15/805,577

(22) Filed: Nov. 7, 2017

(65) Prior Publication Data

US 2018/0372474 A1 Dec. 27, 2018

Related U.S. Application Data

(60) Provisional application No. 62/418,671, filed on Nov. 7, 2016.

(51) Int. Cl.
*G01B 7/00* (2006.01)
*G01B 7/16* (2006.01)
(Continued)

(52) U.S. Cl.
CPC .............. *G01B 7/16* (2013.01); *A41D 1/002* (2013.01); *A41D 13/0015* (2013.01);
(Continued)

(58) Field of Classification Search
CPC ...... G01B 7/16; A41D 1/002; A41D 13/0015; A41D 31/02; A41H 1/02; A43B 3/0005; A43B 5/00; A43B 13/12
(Continued)

(56) References Cited

U.S. PATENT DOCUMENTS 3,968,320 A    7/1976  Herber et al.
4,363,322 A *  12/1982 Andersson ........ A61F 13/00029
                                                              604/359
(Continued)

FOREIGN PATENT DOCUMENTS

EP         1 637 046 A3    5/2008
WO      WO1998/44819      10/1998
(Continued)

*Primary Examiner* — Max H Noori
(74) *Attorney, Agent, or Firm* — Tsircou Law, P.C.

(57) ABSTRACT

Athletic apparel, including compression garments and athletic footwear, is disclosed as capable of monitoring the wear of compression fabric and/or cushioning material by attaching a performance gauge onto the apparel. The performance gauge includes microcapsules that contain a colorless dye and/or a co-reactant, wherein the microcapsules can breakdown in concert with the wear and degradation of the compression fabric or cushioning material, thereby allowing the dye and co-reactant to mix and produce color indication. As the wear of the fabric and cushioning material increases, more microcapsules breakdown resulting in a progression of color change visible through additional layers on the performance gauge, or by the fabric and/or cushioning material. The microcapsules can be engineered to breakdown based on any variation of factors that correspond to the degradation of compressive fabric and cushioning material, including shear force, tension, impact force, and/or exposure to high temperature and water.

20 Claims, 6 Drawing Sheets

(51) Int. Cl.
| | |
|---|---|
| *A41D 1/00* | (2018.01) |
| *A41D 13/00* | (2006.01) |
| *A61B 5/00* | (2006.01) |
| *B32B 27/12* | (2006.01) |
| *A43B 1/00* | (2006.01) |
| *A43B 23/02* | (2006.01) |
| *A41D 31/02* | (2019.01) |
| *A41H 1/02* | (2006.01) |
| *A43B 3/00* | (2006.01) |
| *A43B 5/00* | (2006.01) |
| *A43B 13/12* | (2006.01) |

(52) U.S. Cl.
CPC .............. *A41D 31/02* (2013.01); *A41H 1/02* (2013.01); *A43B 1/0027* (2013.01); *A43B 3/0005* (2013.01); *A43B 23/0225* (2013.01); *A43B 23/0235* (2013.01); *A61B 5/00* (2013.01); *B32B 27/12* (2013.01); *A43B 5/00* (2013.01); *A43B 13/12* (2013.01)

(58) Field of Classification Search
USPC .......................................................... 73/763
See application file for complete search history.

(56) References Cited

U.S. PATENT DOCUMENTS

| | | | |
|---|---|---|---|
| 5,040,313 A * | 8/1991 | Simjian | A43B 3/00 36/114 |
| 5,293,648 A | 3/1994 | Finley | |
| 6,389,711 B1 * | 5/2002 | Polegato | A43B 7/08 36/3 R |
| 6,578,291 B2 | 6/2003 | Hirsch et al. | |
| 6,922,916 B1 | 8/2005 | Potter | |
| 7,353,770 B2 | 4/2008 | Sanguinetti | |
| 7,698,101 B2 | 4/2010 | Alten et al. | |
| 8,734,272 B2 | 5/2014 | Tutmark | |
| 9,578,908 B2 | 2/2017 | Berns et al. | |
| 2001/0049890 A1 | 12/2001 | Hirsch et al. | |
| 2006/0059603 A1 | 3/2006 | Peng et al. | |
| 2008/0083286 A1 * | 4/2008 | Danowski | G01L 1/24 73/774 |
| 2009/0064919 A1 | 3/2009 | Greenwald | |
| 2010/0012017 A1 | 1/2010 | Miller | |
| 2013/0206316 A1 * | 8/2013 | Liu | B32B 37/24 156/62.2 |
| 2013/0319292 A1 * | 12/2013 | Kusama | C09D 5/00 106/287.24 |
| 2014/0062703 A1 | 3/2014 | Purks et al. | |
| 2014/0137965 A1 * | 5/2014 | Truitt | A41D 27/08 137/596 |
| 2014/0143881 A1 * | 5/2014 | Boday | G06F 21/87 726/26 |
| 2014/0148741 A1 * | 5/2014 | Moran | A41D 13/0015 601/84 |
| 2014/0363091 A1 * | 12/2014 | Boday | G01N 21/6447 382/218 |
| 2015/0040282 A1 | 2/2015 | Longinotti-Buitoni et al. | |
| 2017/0089779 A1 * | 3/2017 | Dantus | G01L 5/0052 |
| 2017/0122855 A1 * | 5/2017 | Dantus | A63B 71/08 |
| 2018/0037749 A1 * | 2/2018 | Wilson | C09D 7/63 |

FOREIGN PATENT DOCUMENTS

| | | |
|---|---|---|
| WO | WO2004/055758 | 7/2004 |
| WO | WO2013/176755 | 11/2013 |

* cited by examiner

PERFORMANCE GAUGE FOR FABRIC AND CUSHIONING MATERIAL

CROSS REFERENCE TO RELATED APPLICATION

This application claims the benefit of U.S. Provisional App. No. 62/418,671, filed Nov. 7, 2016, which is incorporated by reference.

FIELD OF THE INVENTION

The present invention relates generally to fabric and cushioning material, and more specifically, to a performance gauge for high performance fabric used in athletic apparel, shapewear, and so on, and to a performance gauge for cushioning material used in high performance footwear, such as athletic shoes, hiking shoes, and so on.

BACKGROUND OF THE INVENTION

Athletic performance apparel has become increasingly popular as they provide specific benefits for a given physical activity. Some examples of such apparel include compression clothing, sports bras, yoga pants, running shoes, and cross-training shoes. For compression clothing, the principal functionality is to maintain a skin-tight fit, and can further apply pressure to parts of the body to prevent injury and improve blood flow during exercise, providing the benefit of an improved performance and recovery. For running shoes, the principle functionality is to provide sufficient stability and cushioning to absorb shock and to reduce the magnitude of localized pressure peaks, thereby providing the benefit of reduced stress to the foot and improved performance.

Athletic apparel is expected to develop further in the future, adding more functionality and benefits. This includes compression athletic wear that is customized to the athlete's dimensions and type of activity. With the increase in hyper-engineered apparel costs, consumers will demand perfection and want to know definitively when their apparel is deteriorating in performance. Fabric performance is also important in other contexts, such as bras, shapewear, and mattresses.

High performance fabric is made out of synthetic polymeric fibers. The unique material properties of polymeric fibers contribute to the desired performance of the fabric for athletic activity and/or support. Polymers are compliant, i.e., have a low elastic modulus, which contributes to the fabric's flexibility. Upon being stretched, polymers can store energy, which allows the polymeric fibers to return to their original state with force after an athletic movement.

However, the polymeric fibers lose their elastic recovery over time by undergoing irreversible deformation. The fibers stretch over time, but without storing energy that would allow the fibers to return to their original state. Therefore, the clothing loses its shape and the compressive performance of the fibers is compromised. Fatigue deformation of polymers is controlled by a viscoelastic phenomenon called creep and stress relaxation. On a micro scale, with continuously applied moderate force, the polymer chains slowly swim around each other and align with the direction of force. On a macro scale, the fibers stretch and thin out. Eventually, as the cross-sectional area of the fibers decreases, the polymer chains can no longer accommodate the force and bonds within the chains, and cross-links between the chains will break. Thus, the user may continue to use such apparel without knowing that its benefit has run its course due to prolonged exposure to a variety of factors, including, but not limited to, stretching, shear force, high temperature, and water.

For high performance footwear, the cushioning material embedded in the midsole, outsole, and heel help redistribute the ground resultant force acting on the body during physical activities such as walking, running, or jumping. The cushioning material used in the midsole can vary over different types, such as foam materials or polyurethane, while the outsole and heel are typically made from rubber. Similar to the polymers in high performance fabrics, the cushioning material in high performance footwear, when receiving a pressure load, can store energy when being elastically deformed, and thus allowing for an elastic recovery to its original shape when the pressure load is removed.

However, also similar to the fibers found in high performance fabrics, the cushioning in the shoe does not store all the energy from the ground resultant pressure force in its deformed state, but instead some energy is released as heat. Thus over time, the recurrence effects of activity and heat build-up within the cushioning causes the material to eventually denature, and thereby leading to a reduction in the elasticity of the cushioning material, ie stiffening. Moreover, the impact forces and friction forces, along with heat and water exposure, may result in a reduction in the thickness on the outsole and heel, thereby also reducing the shock absorbency and cushioning for the wearer. Thus, similar to high performance fabric, a user may continue to use a high performance footwear without realizing that benefits, such as absorbing shock and distributing stress points, are no longer available.

It should, therefore, be appreciated that there is a need for fabric and cushioning material that can each accurately alert the user when it is ceasing to perform adequately, particularly when it is a component of athletic apparel, wherein such alerting mechanism will be readily indicative and not be overly intrusive nor aesthetically displeasing to the apparel.

SUMMARY OF THE INVENTION

Briefly, and in general terms, a performance gauge for athletic apparel material, including footwear, is provided, wherein microcapsules are used to visually cue loss of performance in fabric and cushioning material.

More specifically, in an exemplary embodiment, the performance gauge is built into apparel, as a tag or stamp below the waist or neckband of a garment, inside of a shoe opening, on the outsole or heel of a shoe, or in any other suitable position. The performance gauge will indicate wear by changing color gradually as the fabric deteriorates, or as the shoe cushioning material deteriorates and/or stiffens. The performance gauge could be any shape, including for example, a short strip that changes color gradually; a round shape that changes color clockwise; or three or four chevrons that change color sequentially from left to right.

In an exemplary embodiment, the performance gauge uses microcapsule breakdown to remove a barrier between a colorless dye and its co-reactant activator, allowing for gradual color change as more microcapsules are ruptured.

In a detailed aspect of an exemplary embodiment, the microcapsules are disposed in a layer with a binder that is affixed to the fabric and/or cushioning material.

In another detailed aspect of an exemplary embodiment, an indicating substrate is further provided, wherein said indicating substrate can be a laminate or coating.

In another detailed aspect of an exemplary embodiment, the microcapsules may be sprayed, coated, or immersed into the fibers of the garment, or may be mixed into a laminate or plastisol ink.

In another detailed aspect of an exemplary embodiment, the microcapsules may be sprayed, coated, or immersed into the material of the shoe sole, heel, and/or insole In another exemplary embodiment, the microcapsules contain a co-reactant that activates color formation upon contact with a halochromic material disposed about the performance gauge.

In yet another exemplary embodiment, the microcapsules contain a pre-activated dye, such that the microcapsules display the color of the dye. The performance gauge will indicate wear of the fabric and/or cushioning material as the initial color gradually fades away resulting from microcapsule breakdown and the progressive washing away of the released dye.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which:

FIG. 6 depicts a laminate/coating layer, microcapsules embedded in a binder layer, a cushioning material about the heel, and the progression of microcapsules rupturing due to the cushioning material stiffening.

DETAILED DESCRIPTION OF THE PREFERRED EMBODIMENTS

Figure 1A:
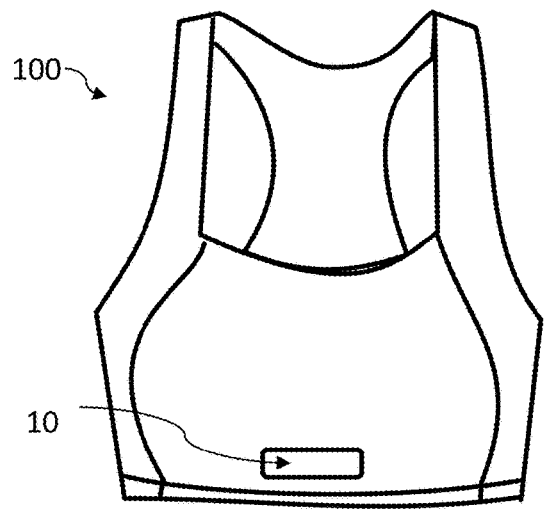
FIG. 1A is a front perspective view of a sports bra having a performance gauge in accordance with the present invention.
Figure 1B:
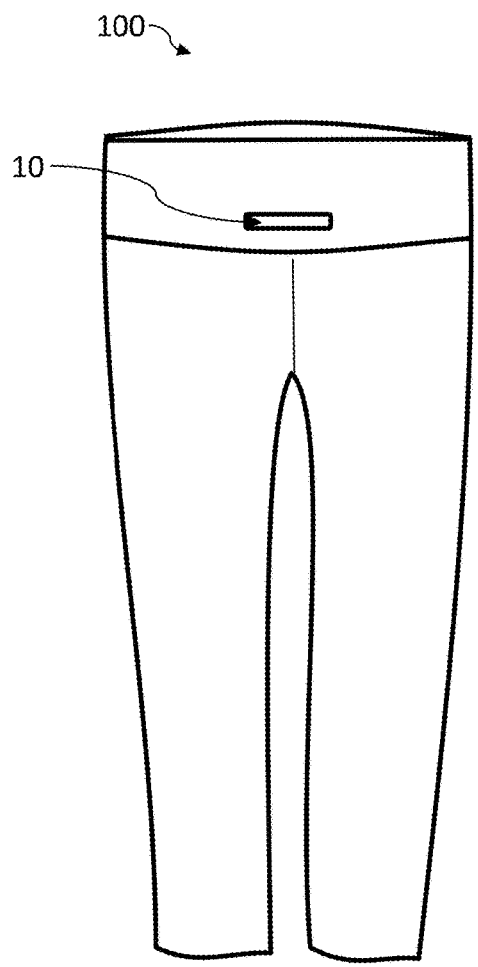
FIG. 1B is a rear perspective view of athletic pants having a performance gauge in accordance with the present invention.

Referring now to the drawings, and particularly FIGS. 1A-1B, there is shown athletic apparel 100 bearing a performance gauge 10 for fabrics. The performance gauge 10 measures the wear of compression fabrics by displaying color change in a tag, stamp, or other similar form. The performance gauge 10 can be affixed to apparel in any location, such as in the waistband of a pair of pants, the neckband of a shirt, or about the opening of a shoe. FIG. 1A shows a sports bra, wherein a rectangular performance gauge 10 is on the lower front portion of the garment. FIG. 1B shows athletic pants, wherein a rectangular performance gauge 10 is on the upper back portion of the garment, specifically the rear end of the waistband.

The performance gauge 10 may be used on any appropriate athletic apparel, e.g., compression shorts and shirts, bras, shapewear, yoga pants, and footwear with a compressive footwear opening. The performance gauge can also be used to indicate wear on a mattress, or anywhere the performance of fabric is important. The size of the performance gauge can be optimized to allow the indicator to be readily indicative while limiting the amount of specialized material required. The performance gauge may change color gradually, be a round shape that changes color clockwise, be three or four chevrons that change color sequentially from left to right, or any configuration and/or shape desired. Placement of each performance gauge will ideally account for areas of critical performance, such as the bicep or calve, and also account for visual convenience and/or aesthetic.

Figure 2:
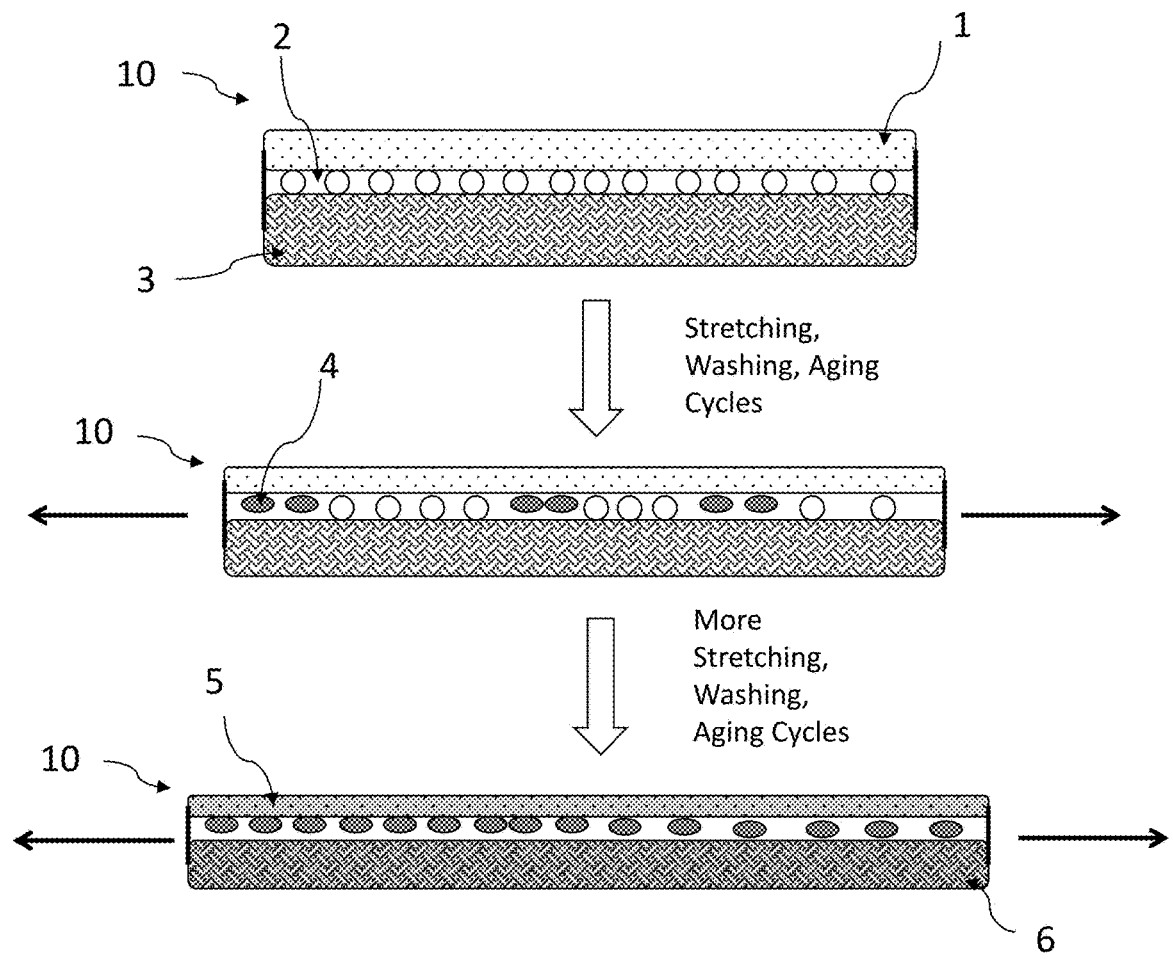
FIG. 2 is a view of a performance gauge in accordance with the present invention, showing its behavior over time when used on fabrics, depicting a laminate/coating layer, microcapsules embedded in a binder layer, a fabric layer, and the progression of microcapsules rupturing due to the fabric stretching.

FIG. 2 illustrates an exemplary embodiment of a performance gauge 10 in accordance with the present invention, showing its behavior over time, when used on fabrics. At the top is a substantially new performance gauge 10, which comprises of a microcapsule and binder layer 2, and a laminate/coating layer 1, both covering the fabric 3. Over time, stretching, washing, exposure to human sweat, and/or aging causes the microcapsules 4 to rupture, releasing a colorless dye and possibly a co-reactant from within, activating color formation (further described below). Thus, breakdown of the microcapsules 4 removes the barrier between colorless dye 30 and its co-reactant activator 31, allowing for a gradual color change as more microcapsules 4 are ruptured. Additional stretching, washing, exposure to human sweat, and/or aging will result in the laminate/coating 1 and/or fabric 3 to absorb additional color 5,6 as more microcapsules 4 rupture.

As aforementioned, activated dye may be absorbed by the fibers of the fabric 3,6 and/or the laminate/coating 1,5. If strong bonding of the activated dye to the fiber is necessary, this can be accomplished with heat during a normal washing/drying cycle. An additive may further be used to promote curing and bonding to the fabric 3. The activated dye may also be suspended between the fabric 3 and laminate/coating 1, wherein the laminate/coating layer is transparent to enable color visibility.

A binder layer 2 with embedded microcapsules 4 may be affixed to the fabric to prevent the microcapsules 4 and/or released dye from washing away during wash cycles. The binder layer 2 may also ensure that there is suitable mechanical stress transfer between the fibers of the fabric 3 and microcapsules 4 during stretching, thereby enhancing the fabric wear predictability. The proximity of the binder layer 2 to the fabric 3 also allows for color absorption of the activated dye. The binder layer 2 can be of any suitable textile. Alternative embodiments of the performance gauge 10 may not include a binder layer 2, but instead the microcapsules 4 can be sprayed, coated, or immersed onto the fibers of the garment 100, or may be mixed into a plastic laminate/coating 1 or plastisol ink.

An indicating substrate may also be provided with the performance gauge 10. The indicating substrate can be a small region of garment fibers, external fibers sewn into the garment, plastisol printed onto the garment, and/or plastic laminated/coated onto the garment. The purpose of the indicating substrate is to absorb released dye and display the color change. Although the laminate/coating 1 or fabric 3 may also serve this purpose, the absorption of the dye may not be to a satisfactory degree and additional material (fiber or plastic) may be necessary for the performance gauge 10 to better display the color change. For example, external natural fibers (known to absorb dye better than synthetic fibers commonly used in athletic wear) may be sewn into the performance gauge region of the garment with the sole purpose of absorbing dye. The laminate/coating 1 may act as an indicating substrate.

Additionally, the laminate/coating 1 may serve several other purposes. It can attenuate microcapsule 4 breakdown from stimulation and washing in favor of stretching and human sweat breakdown. This is achieved by disposing a rubbery laminate/coating over the sensing region of the garment (where the performance gauge is located), which will absorb impact damage in order to increase the effect of fiber stretch on microcapsule 4 breakdown. The laminate/coating 1 may also serve to prevent the washing away of released dye and co-reactant during a wash cycle, by regulating the rate of water transfer to the sensing region such that the microcapsules 4 are not oversensitive to wash cycles (further described below).

The laminate/coating 1 may include a hydrophobic film that is microporous, i.e., having openings from roughly 1-50 μm in diameter. This allows individual water vapor molecules to pass through, while blocking the passage of larger water droplets. The size of the pores can also selectively allow small water molecules to pass through without allowing larger dye molecules to pass through. The size of pores, or lack thereof, of hydrophobic films regulates the type or phase of chemicals that are allowed to pass through. In another embodiment, the laminate/coating 1 may include a hydrophilic film without pores that permits water vapor transport via diffusion through the film. Hydrophilic films should be solid and only permit passage of water via diffusion. The driving forces for diffusion are differences in humidity and temperature either between the sensing region of the garment and the external climate, or between the sensing region of the garment 100 and the human body.

The laminate/coating 1 should be made of polyurethane, PTFE, or similar material. The thickness of the laminate/coating 1 controls water vapor transmission rate and the degree of impact absorption. The film can have both hydrophobic and hydrophilic components to further control the type of species that can pass through and the rate at which they pass. Contamination of PTFE with oil, sweat, and chemicals can diminish the hydrophobicity of PTFE, thus allowing increased permeability of water to the sensing region with extended use of the garment. PTFE film can be coated with its own protective film to sustain hydrophobicity, or this effect can be exploited to further increase microcapsule 4 breakdown with extended use of the garment 100.

The laminate/coating 1 may also comprise of halochromic material that is activated by a co-reactant contained within the microcapsules 4, or by contact with detergent, such as during a wash cycle, wherein such activation results in color indication (further described below). As aforementioned, membranes in the laminate/coating 1 can regulate detergent contact with the halochromic material.

Figure 3:
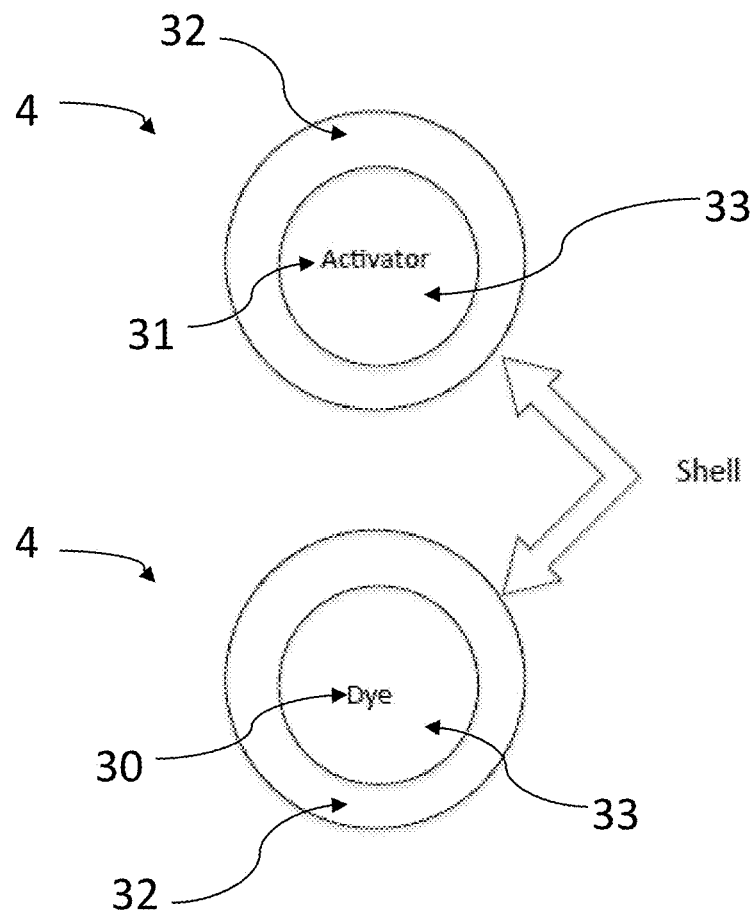
FIG. 3 illustrates microcapsules in accordance with the present invention, depicting an outer shell, an inner volume, dye located in one inner volume, and a co-reactant located in another inner volume.

FIG. 3 shows a detailed view of the microcapsules 4, comprising an inner volume 33 surrounded by an outer shell 32. Separate microcapsules 4 may house dye 30 and/or co-reactant activators 31 for that dye, thereby separating a colorless (inert) dye 30 from its respective co-reactant 31. In the absence of the microcapsule barrier 4, the co-reactant 31 will activate the dye 30 and cause it to change color, e.g., from clear to any desired color. The microcapsules 4 may contain one type of dye color or a variety of dye colors used in concert to indicate a spectrum of damage. The embodiment disclosed in FIG. 3 represents a two-part leuco dye system wherein one set of microcapsules 4 contains colorless dye 30 and the other set of microcapsules contains the respective co-reactant 31 that will initiate color change. Alternatively, one set of microcapsules can be used wherein the microcapsules 4 contain only the co-reactant 31, which upon release activate a halochromic material contained within a laminate/coating 1, and thereby initiate color indication. In another embodiment, these microcapsules 4 may only contain the colorless dye 30, which are activated by an environmental or detergent stimulus upon release to initiate color indication.

In yet another embodiment, the microcapsules 4 will contain pre-activated dye, such that the microcapsules, and therefore performance gauge, will initially display the color of the dye. In this alternate embodiment, the performance gauge lacks a laminate/coating layer, thus enabling the released pre-activated dye, from microcapsule breakdown due to wear of the fabric, to be susceptible of being washed away. The performance gauge will thereby indicate wear of a fabric through the progressive washing away of the dye and gradual uncovering of the color of the base apparel.

The microcapsules 4 are designed to break down over time from the same factors that would damage athletic apparel 100 over time, which as aforementioned include, among other factors, stretching, washing, exposure to human sweat, and/or aging. In the exemplary embodiment, as more microcapsules 4 rupture, more dye 30 will be activated and the color change will be more pronounced.

The stretching of fibers will directly connect the garment 100 fiber condition to the microcapsule breakdown since stretching of the fibers will decrease the cross-sectional area of the fibers of the fabric 3 or laminate/coating 1, thereby subjecting the microcapsules 4 to pressure and shear forces, causing the microcapsules 4 to rupture over time. The friction between textile fibers during movement can also serve to break down the outer shell 32 of the microcapsules 4.

The microcapsules 4 may further be designed to breakdown more slowly over a period of high-temperature wash cycles, or designed to dissolve more slowly due to exposure to detergent or sweat. Thus, by combining different microcapsule 4 designs, the performance gauge 10 can depict a color change that favors a given fabric breakdown stimulus, such as athletic activity and/or wash cycles.

The size of the microcapsules can be approximately 100 µm or less. Microcapsule size is one of a number of parameters that affects the release rate of the encapsulated dye and co-reactants. For example, 10-micron microcapsules will release the inner volume 33 ingredient faster than 100-micron microcapsules, given the same external loads. Thus, the performance gauge can be tailored to produce color change in correlation with the loss of performance integrity of a given garment 100 by specifying the size and number of microcapsules 4, the thickness of the outer shell 32, and the ratio of dye capsules 30 to co-reactant capsules 31.

Embodiments of the present invention can be considered a hybrid of direct and indirect sensors for wear of athletic apparel. It is direct in the respect that the stretching of fibers will act as a stimulus to color change via microcapsule breakdown. Indirect sensing is also achieved via microcapsules designed to melt slowly over a period of high-temperature wash cycles or dissolve slowly due to exposure to detergent or sweat. The performance gauge can contain a combination of the capsules mentioned above so that it is designed to change color slowly over a period of fatigue via athletic activity and/or wash cycles.

Figure 4A:
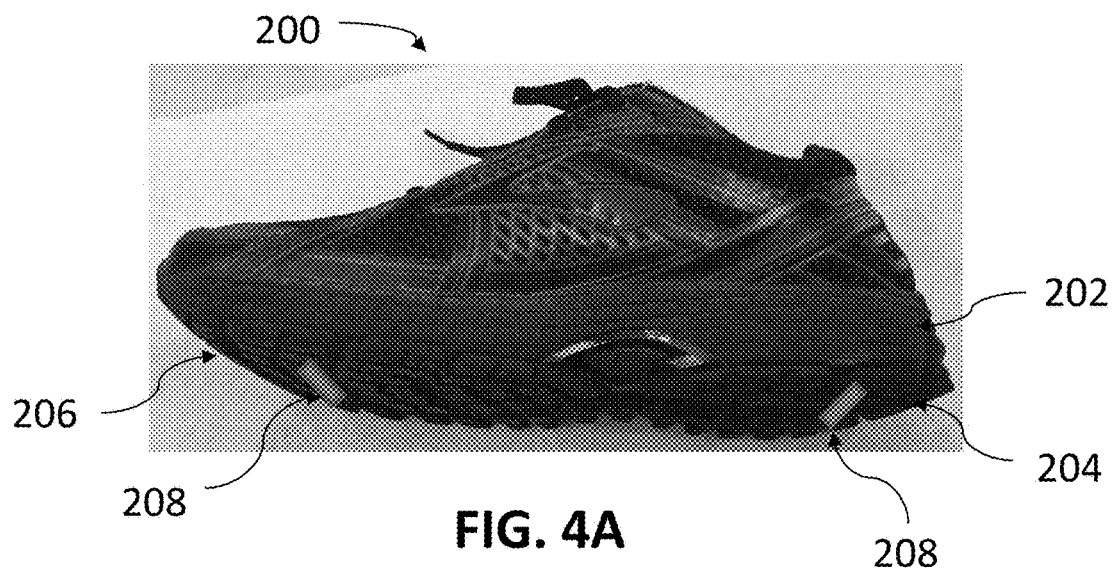
FIG. 4A is a side perspective view of a footwear assembly having multiple performance gauges in accordance with the present invention, depicting an outsole, a midsole, a heel and two performance gauges.
Figure 4B:
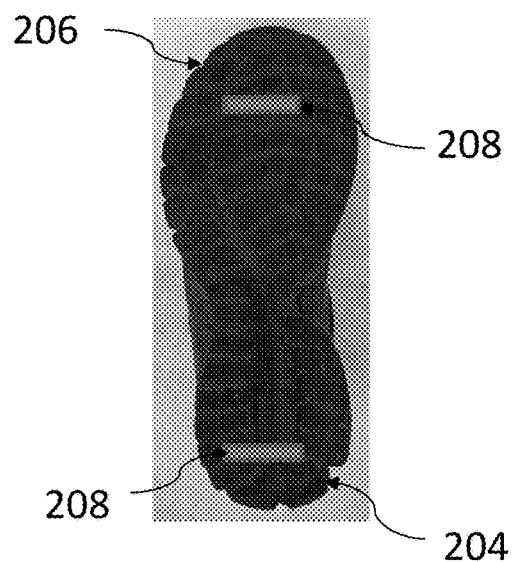
FIG. 4B is a bottom perspective view of the footwear assembly in FIG. 1A, depicting the outsole and heel, each with a corresponding performance gauge
Figure 5:
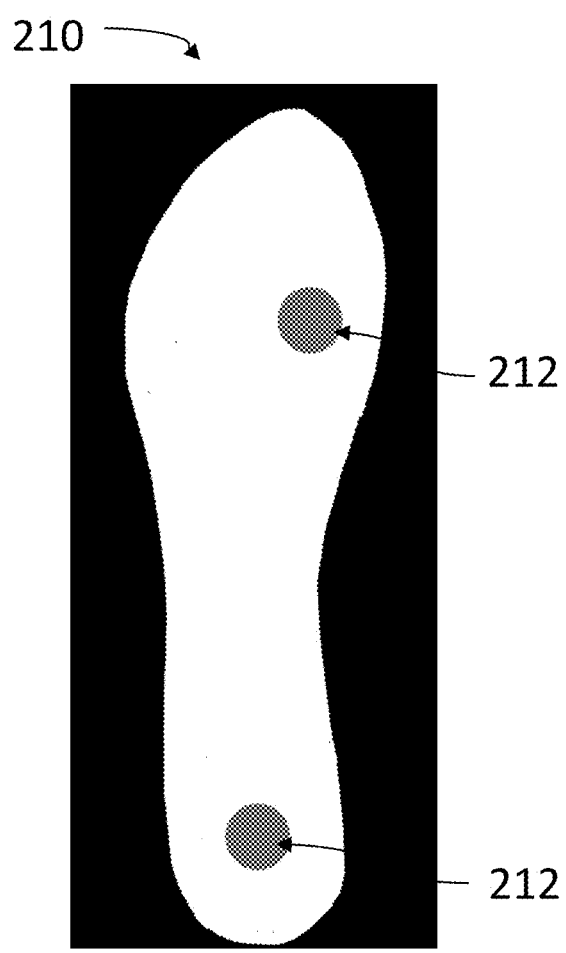
FIG. 5 is a top perspective of a shoe insole with two performance gauges

Referring now to FIGS. 4A-4B, there is shown a high performance footwear 200 bearing a performance gauge 208. The performance gauge 208 measures the deterioration of cushioning material in a footwear assembly by displaying color change in a tag, stamp, or other similar form. The performance gauge 208 can be affixed to any location on the outsole 206, heel 204, or insole. In an alternative embodiment, the performance gauge 208 can be attached to a midsole 202. Referring now to FIG. 5, there is shown a top perspective of the insole 210 of the footwear 200 wherein a circular performance gauge 212 is located on the ball and heel locations of an insole 210.

The performance gauge 208, 212 may be used on any appropriate footwear, e.g., high performance shoes such as running and cross-training shoes, hiking shoes, outdoor shoes, and so on. The performance gauges 208,212 can contain similar characteristics as described when used for fabrics, including size, shape(s), and color changing progression. Placement of each performance gauge 208,212 will ideally account for areas of high impact and stress, such as the heel and ball of the foot, and also account for visual convenience or aesthetic appeal.

Figure 6:
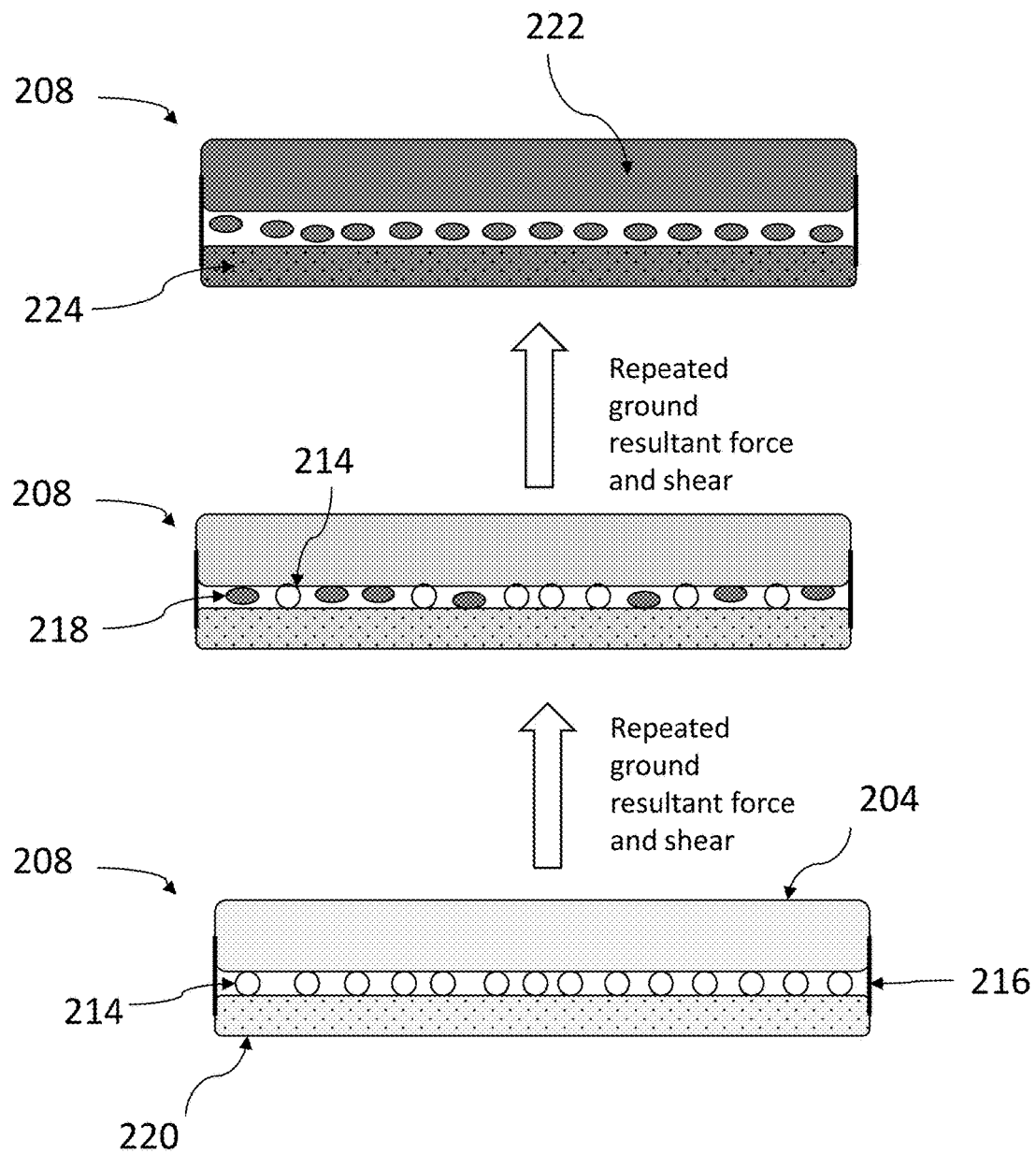
FIG. 6 is a view of a performance gauge in accordance with the present invention, showing its behavior over time when used on cushioning material about a heel.

FIG. 6 provides an exemplary embodiment of a performance gauge 208 in accordance with the present invention, showing its behavior over time when attached to the heel 204 of a footwear, which contains a cushioning material. At the bottom is a substantially new performance gauge 208. The sensing region on the heel 204 is covered by microcapsules 214 embedded within a binder layer 216, followed by a laminate/coating layer 220. As aforementioned for fabric performance gauges, the binder layer 216 helps in preventing the microcapsules from being displaced away from the sensing region. Over time, impact forces, specifically ground resultant forces due to walking, running, and jumping, and impact forces such as from a user's foot, along with factors such as friction force, heat and water exposure causes the microcapsules 214 to rupture, releasing dye and possibly a co-reactant from within, activating color formation 218. After prolonged exposure to ground resultant forces, other impact forces, friction, water, and heat, the laminate/coating 224 and/or heel 222 absorb additional color as more microcapsules 214 rupture. In an alternate embodiment, the color activated dye will be suspended between the outsole 206 and/or heel 204, and the laminate/coating 220, wherein the laminate/coating is transparent, allowing for color visibility. In yet another embodiment, an interface material may be located between the performance gauge and the outsole 206 and/or heel 204, so as to prevent color absorption to the shoe material in areas that would lower the aesthetic appeal.

As mentioned previously for performance gauges used in fabrics, the laminate/coating 220 can act as the color changing substrate and may provide other purposes, such as minimizing the cushion degradation due to water or sweat exposure. The laminate/coating may also come with a hydrophobic or hydrophilic film which can regulate the water transfer to the microcapsules. This can also help in preventing the dye and/or co-reactants from being washed away if the footwear is exposed to water.

The performance gauge for cushioning material will contain microcapsules as previously described in FIG. 3 (reference character 4). The size and number of the microcapsules, outer shell thickness, and the ratio of the dye capsules to co-reactant capsules may similarly be varied so that noticeable color change correlates accurately with a loss of performance integrity of a given footwear 200. Moreover, also similar to the performance gauge used for fabrics, the microcapsules can be a two-part leuco dye system wherein one set of microcapsules 4 contain a colorless dye 30 and another set of microcapsules contains the respective co-reactant 31. The microcapsules 208, 212 may also contain one type of dye color or a variety of dye colors used in concert to indicate a spectrum of damage. Alternatively, the performance gauge may contain one set of microcapsules that contain only a co-reactant 31, and a laminate/coating 1 comprising a halochromic material that is activated by the co-reactant upon release from the respective microcapsules 4, thereby producing color indication.

In yet another embodiment, the microcapsules 4 will contain pre-activated dye, such that the microcapsules, and therefore performance gauge, will initially display the color of the dye. In this alternate embodiment, the performance gauge lacks a laminate/coating layer, thus enabling the released pre-activated dye, from microcapsule breakdown due to wear of the cushioning material, to be susceptible of being washed away. The performance gauge will thereby indicate wear of a cushioning material through the progressive washing away of dye and gradual uncovering of the color of the base footwear.

In the exemplary embodiment, the binder layer can be of suitable material such as textile, foam and/or rubber. In addition to the binder layer, the microcapsules can be built into the footwear by being coated onto or immersed into the material shoe sole, heel, and/or insole. These microcapsules are also designed to break down over time from the same factors that would damage the cushioning material over time, which as aforementioned include among others, ground resultant forces, impact forces from a user's foot, friction forces, heat, and exposure to water. Similar for fabrics, in the exemplary embodiment, as more microcapsules rupture, more dye will be activated and the color change will be more pronounced.

Ground resultant forces and other impact forces will be a major stimulus in directly correlating color change to the wear of the cushioning material, since the force applied to the microcapsules will be directly related to the stiffness of the cushioning material. As the cushioning material stiffens and loses its ability to absorb shock over time, it will transfer more shock forces to the user and the microcapsules, thereby further accelerating the microcapsule breakdown. The direct relationship between cushioning material deterioration and microcapsule rupture can be further strengthened by engineering the microcapsule to contain a fatigue strength that correlates with the fatigue strength of the corresponding cushioning material.

It should be appreciated from the foregoing that the present invention provides a performance gauge for compression fabric and cushioning material, which uses dye or halochromic material with corresponding co-reactants separated by microcapsules, that break down in concert with the degradation of the fabric and cushioning material, thereby signaling the loss of functionality caused by mechanical damage to the material. Thus, the invention lets the user know definitively when the fabric or cushioning material is deteriorating in performance.

The present invention has been described above in terms of presently preferred embodiments so that an understanding of the present invention can be conveyed. However, there are other embodiments not specifically described herein for which the present invention is applicable. Therefore, the present invention should not to be seen as limited to the forms shown, which is to be considered illustrative rather than restrictive.

Although the invention has been disclosed in detail with reference only to the exemplary embodiments, those skilled in the art will appreciate that various other embodiments can be provided without departing from the scope of the invention, to include any and all combination of features discussed herein.

What is claimed is:

1. A performance gauge that provides for monitoring fabric degradation and/or cushioning material degradation, comprising:
   a body that can be affixed to fabric and/or cushioning material;
   a first plurality of microcapsules embedded within said body, each microcapsule of the first plurality of microcapsules having (a) a first outer shell encompassing a first inner volume and (b) a dye that is contained within said first inner volume, wherein said dye can escape the first inner volume upon rupture of the first outer shell; and
   a second plurality of microcapsules embedded within said body, each microcapsule of the second plurality of microcapsules having (a) a second outer shell encompassing a second inner volume and b) a co-reactant that is contained within said second inner volume, wherein said co-reactant can escape the second inner volume upon rupture of the second outer shell, and said co-reactant will activate with the dye upon contact therewith, to produce color indication.

2. The performance gauge defined in claim 1, wherein the first outer shell for the first plurality of microcapsules and the second outer shell for the second plurality of microcapsules will progressively rupture when subject to pressure and shear forces, impact forces, ground resultant forces, tension, friction, high temperature, and/or exposure to detergent, sweat, or water.

3. The performance gauge defined in claim 1, wherein the body includes a layer of textile, foam, or rubber, and further comprises a laminate or coating layer that absorbs and displays the color of the activated dye, said laminate or coating layer further comprising a) a hydrophobic film that is microporous and/or b) a hydrophilic film that is non-porous.

4. A footwear assembly having a footwear body and comprising the performance gauge as defined in claim 1, such that the performance gauge is attached to a cushioning material disposed on the footwear body.

5. An athletic garment that provides for monitoring fabric degradation, comprising:
   a garment body having a compressive fabric, the garment body configured to conform to a portion of the wearer, the garment body having an initial elasticity; and
   a performance gauge secured to the compressive fabric of the garment body, the performance gauge having:
      a first plurality of microcapsules, each microcapsule of the first plurality of microcapsules having (a) a first outer shell encompassing a first inner volume and (b) a substance for color indication that is contained within said first inner volume, such that said substance can escape the first inner volume upon rupture of the first outer shell, such that the first plurality of microcapsules progressively rupture 1) as the elasticity of the garment body reduces from the initial elasticity, and 2) when subject to high temperature and/or exposure to detergent, sweat, or water, such that the progressive rupturing of the first plurality of microcapsules indicate progressive fabric degradation.

6. The athletic garment defined in claim 5, wherein the substance is a dye, the performance gauge further comprising a co-reactant that activates the dye upon contact therewith, to produce color indication.

7. The athletic garment defined in claim 6, wherein the performance gauge further comprises a binder layer affixed to the compressive fabric, and said first plurality of microcapsules are embedded within the binder layer.

8. The athletic garment defined in claim 7, wherein the performance gauge further comprises a laminate or coating layer affixed to the binder layer, the laminate or coating layer having a rubbery material that absorbs impact and/or shock, the laminate or coating layer configured to absorb and display the color of the activated dye.

9. The athletic garment defined in claim 6, further comprising a second plurality of microcapsules, each said microcapsule of the second plurality of microcapsules having (a) a second outer shell encompassing a second inner volume, and (b) the co-reactant contained within said second inner volume, such that said co-reactant can escape the second inner volume upon rupture of said second outer shell, such that the second plurality of microcapsules progressively rupture as the elasticity of the garment body reduces from the initial elasticity, so as to indicate progressive fabric degradation.

10. The athletic garment defined in claim 9, further comprising any combination of microcapsules of the first and second plurality of microcapsules in any size less than or equal to 100 micrometers with any outer shell thickness less than the corresponding microcapsule size.

11. The athletic garment defined in claim 5, wherein the substance is a dye, the garment body further comprising a co-reactant that activates the dye upon contact therewith, to produce color indication.

12. The athletic garment defined in claim 5, wherein the substance is a dye and the first outer shell for the first plurality of microcapsules is transparent, such that the dye is visible therein.

13. The athletic garment defined in claim 5, wherein the substance is a co-reactant activator, the performance gauge further comprising a halochromic material that is activated upon contact with the co-reactant activator, to produce color indication.

14. The athletic garment defined in claim 5, wherein the substance is a dye that is activated upon contact with a detergent stimulus, to produce color indication.

15. The athletic garment defined in claim 5, further comprising any combination of microcapsules of the first plurality of microcapsules in any size less than or equal to 100 micrometers with any outer shell thickness less than the corresponding microcapsule size.

16. The athletic garment defined in claim 5, wherein the performance gauge further comprises at least one indicating substrate that absorbs and displays the color of the activated dye.

17. The athletic garment defined in claim 16, wherein at least one indicating substrate comprises a laminate or coating with a rubbery material that absorbs impact and/or shock.

18. The athletic garment defined in claim 17, wherein at least one indicating substrate comprises a laminate or coating with a) a hydrophobic film that is microporous and/or b) a hydrophilic film that is non-porous.

19. An athletic garment that provides for monitoring fabric degradation, comprising:
   a garment body having a compressive fabric, the garment body configured to conform to a portion of the wearer, the garment body having an initial elasticity; and
   a performance gauge secured to the compressive fabric of the garment body, the performance gauge having:
      a first plurality of microcapsules, each microcapsule of the first plurality of microcapsules having (a) a first outer shell encompassing a first inner volume, and (b) a dye that is contained within said first inner volume, such that said dye can escape the first inner volume upon rupture of the first outer shell, and
      a second plurality of microcapsules, each microcapsule of the second plurality of microcapsules having (a) a second outer shell encompassing a second inner volume, and (b) a co-reactant that is contained within said second inner volume, such that said co-reactant can escape the second inner volume upon rupture of said second outer shell, and said co-reactant will activate with the dye upon contact therewith, to produce color indication, the first and second plurality of microcapsules configured to progressively rupture as the elasticity of the garment body reduces from the initial elasticity, so as to indicate progressive fabric degradation.

20. The athletic garment defined in claim 19, further comprising any combination of microcapsules of the first and second plurality of microcapsules in any size less than or equal to 100 micrometers with any outer shell thickness less than the corresponding microcapsule size.

\* \* \* \* \*